(12) United States Patent
Solanki et al.

(10) Patent No.: US 11,576,570 B2
(45) Date of Patent: Feb. 14, 2023

(54) DETERMINING EYE STRAIN INDICATOR BASED ON MULTIPLE DEVICES

(71) Applicant: QUALCOMM Incorporated, San Diego, CA (US)

(72) Inventors: Vinod Kumar Solanki, Hyderabad (IN); Sathyanarayana Chary Thudimilla, Hyderabad (IN)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 16/691,194

(22) Filed: Nov. 21, 2019

(65) Prior Publication Data

US 2021/0059517 A1 Mar. 4, 2021

(30) Foreign Application Priority Data

Aug. 30, 2019 (IN) .............................. 201921035013

(51) Int. Cl.
| | |
|---|---|
| *A61B 3/10* | (2006.01) |
| *G01J 1/44* | (2006.01) |
| *G16H 15/00* | (2018.01) |
| *A61B 3/00* | (2006.01) |
| *G16H 20/30* | (2018.01) |
| *G06V 20/20* | (2022.01) |

(52) U.S. Cl.
CPC .............. *A61B 3/10* (2013.01); *A61B 3/0058* (2013.01); *G01J 1/44* (2013.01); *G06V 20/20* (2022.01); *G16H 15/00* (2018.01); *G16H 20/30* (2018.01)

(58) Field of Classification Search
CPC . G06F 3/011; G06F 3/01; G06F 3/012; G06F 3/013; G06F 3/014; G06F 3/015; G06F 1/163; G06F 3/03545; G06F 3/0488; G06F 3/017; G06F 3/0346; G06F 3/04815; G06F 3/16; G06F 3/167; G02B 27/017; G02B 27/0172; G02B 2027/0125; G02B 2027/0138; G02B 2027/014; G02B 2027/0187; G02B 27/0081; G02B 30/00; G02B 27/0093; G02B 27/0176; G02B 27/22; G02B 30/40; G02B 2027/0134; G02B 2027/0174; A61B 3/10; A61B 3/0058; G16H 20/30; G16H 15/00; G01J 1/44; G06K 9/00671; H04N 13/344; H04N 13/00; H04N 13/332; H04N 13/383

See application file for complete search history.

(56) References Cited

U.S. PATENT DOCUMENTS

| | | | |
|---|---|---|---|
| 2016/0270656 A1* | 9/2016 | Samec | ........................ A61B 3/10 |
| 2016/0349510 A1* | 12/2016 | Miller | .................. H04N 13/398 |
| 2017/0290504 A1* | 10/2017 | Khaderi | .................. A63F 13/25 |
| 2019/0130622 A1* | 5/2019 | Hoover | .................... G06F 3/005 |
| 2019/0320135 A1* | 10/2019 | Cutler | .................... H04N 7/142 |
| 2020/0057661 A1* | 2/2020 | Bendfeldt | ............ G06V 40/103 |

* cited by examiner

*Primary Examiner* — Hai Phan
*Assistant Examiner* — Anthony D Afrifa-Kyei
(74) *Attorney, Agent, or Firm* — Qualcomm Incorporated

(57) ABSTRACT

Methods and devices determine an eye strain indicator. In one aspect, an augmented reality (AR) device wearable by a user includes an image sensor and a processor coupled to the image sensor. The processor receives image data from the image sensor, determine that a display is within a field of view (FOV) of the AR device, determine an eye strain indicator based on the determination that the display is within the FOV of the AR device, and provide the eye strain indicator to the user.

24 Claims, 7 Drawing Sheets

DETERMINING EYE STRAIN INDICATOR BASED ON MULTIPLE DEVICES

CLAIM OF PRIORITY UNDER 35 U.S.C. § 119

The present application for patent claims priority to Indian Patent Application No. 201921035013 entitled "DETERMINING EYE STRAIN INDICATOR BASED ON MULTIPLE DEVICES" filed Aug. 30, 2019, the disclosure of which is hereby incorporated by reference herein in its entirety.

FIELD

The subject matter disclosed herein relates generally to detecting eye strain based on multiple devices.

BACKGROUND

As more and more digital content is created, users are spending more time viewing and interacting with electronic devices. Such devices include smart phones, desktop computers, laptop computers, televisions, tablets, etc. Electronic devices typically emit light from one or more displays, such as LCD, LED, OLED, and other display types.

Light emitted from electronic device displays often includes so-called "blue light". Blue light is light that is characterized by wavelengths between about 380-500 nm.

Research has shown that excessive exposure to blue light can have harmful or undesirable effects on a user's health. For example, excessive exposure to blue light is believed to cause eye strain and can lead to macular degeneration among other effects. In addition, exposure to blue light can also lead to difficulty sleeping. However, many users are not aware of the amount of blue light they are being exposed to over time.

SUMMARY OF THE DESCRIPTION

In one aspect, an augmented reality (AR) device is wearable by a user. The AR device includes an image sensor; and a processor coupled to the image sensor. The processor is configured to receive image data from the image sensor, determine that a display is within a field of view (FOV) of the AR device, determine an eye strain indicator based on the determination that the display is within the FOV of the AR device, and provide the eye strain indicator to the user.

In another aspect, a method of determining an eye strain indicator includes receiving image data from an image sensor of an augmented reality (AR) device, determining that a display is within a field of view (FOV) of the AR device, determining an eye strain indicator based on the determination that the display is within the FOV of the AR device, and providing the eye strain indicator to a user.

In yet another aspect, an augmented reality (AR) device is wearable by a user. The AR device includes means for generating image data, means for receiving the image data, means for determining that a display is within a field of view (FOV) of the AR device, means for determining an eye strain indicator based on the determination that the display is within the FOV of the AR device, and means for providing the eye strain indicator to the user.

In still another aspect, a non-transitory computer-readable medium includes processor-executable instructions stored thereon. When a processor executes the instructions, the processor is configured to receive image data from an image sensor of an augmented reality (AR) device, determine that a display is within a field of view (FOV) of the AR device, determine an eye strain indicator based on the determination that the display is within the FOV of the AR device, and provide the eye strain indicator to a user.

Other features and advantages will be apparent from the accompanying drawings and from the detailed description.

DETAILED DESCRIPTION

The word "exemplary" or "example" is used herein to mean "serving as an example, instance, or illustration." Any aspect or embodiment described herein as "exemplary" or as an "example" is not necessarily to be construed as preferred or advantageous over other aspects or embodiments.

In one aspect, an augmented reality device captures image data using an image sensor. The image sensor transmits the image data to a processor. The processor determines whether one or more displays are within a field of view (FOV) of the device. The processor also determines an amount of time that the one or more displays were within the FOV of the device during a monitoring period of time (e.g., during 24 hours or another suitable period of time). The processor then determines an eye strain indicator based on the amount of time that the one or more displays were within the FOV of the device. The processor then provides the eye strain indicator to the user, such as by displaying the eye strain indicator on a display of the AR device, by providing an audio or haptic alert using the AR device, or by transmitting the eye strain indicator to a device that is separate from the AR device. The eye strain indicator may alert the user to an amount of eye strain and/or blue light that the user has been exposed to during the monitoring period. The user may then take corrective action, such as by blinking more often, avoiding or minimizing the use of electronic devices for a period of time, turning on a blue light filter or a "night mode" to reduce an amount of blue light emitted by the display(s), and/or any other suitable action. In such a manner, the user's eye health may be enhanced.

Figure 1:
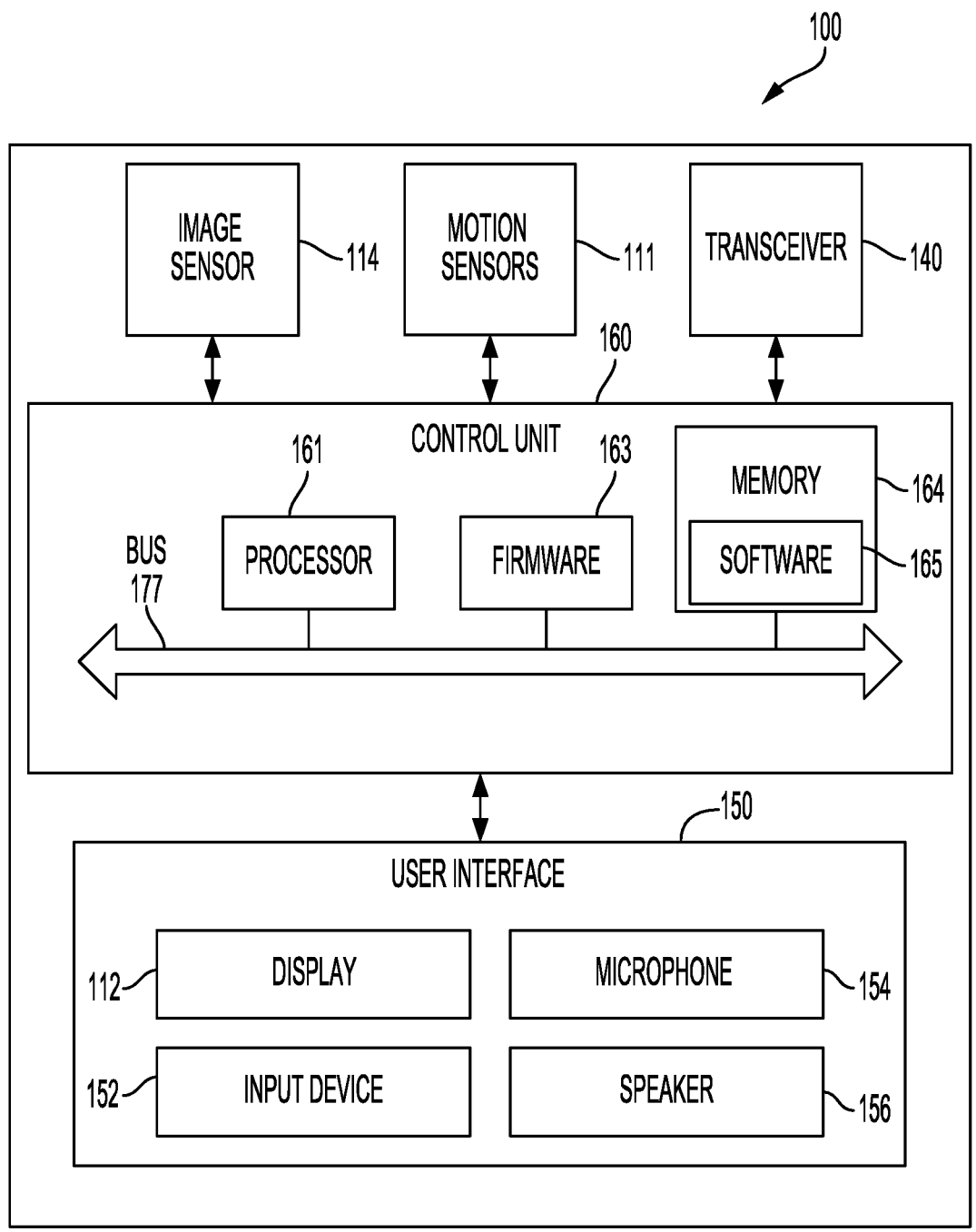
FIG. 1 is a block diagram of a device that may incorporate aspects of the disclosure.

FIG. 1 is a block diagram illustrating an example device 100. In the example shown in FIG. 1, the device 100 is an augmented reality (AR) device 100. The device 100 may be a device that is wearable over the eyes of the user, such as smart eyeglasses, headgear, or the like. Alternatively, the device may be worn or held by the user in such a way that the device is able to detect objects within the field of view of the user. The device 100 may include a control unit 160 that includes a processor 161 and a memory 164 coupled to one or more busses 177 or signal lines. Control unit 160 can be configured to implement methods of performing object detection as described herein. For example, the control unit 160 can be configured to implement functions of device 100 for detecting displays within a field of view of the device 100.

The device 100 can include a means for capturing an image and generating resulting image data, such as image sensor 114. The image sensor 114 may be incorporated into a front-facing camera in some aspects. The device 100 may optionally include motion sensors 111, such as accelerometers, gyroscopes, electronic compass, or other similar motion sensing elements. In one embodiment, image sensor 114 produces an input image for the object detection system 170 as described herein. Furthermore, as an illustrative example, memory 164 may store instructions which when executed by processor 161, can create regions in the input image, can select according to probability, a particular region, can analyze properties of regions, and update probabilities for the regions.

The device 100 may further include a user interface 150 that includes a means for displaying an augmented reality image, such as the display 112. The user interface 150 may also include an input device 152, such as a keyboard, keypad, gesture recognition system, or other input device through which the user can input information into the device 100. The user interface 150 may also include a microphone 154 and speaker 156. Device 100 may include other components not illustrated in FIG. 1, such as a satellite position system receiver, power device (e.g., a battery), as well as other components typically associated with portable and non-portable electronic devices.

The device 100 may include a transceiver 140 that may communicate via one or more wireless communication links through a wireless network based on or otherwise supporting any suitable wireless communication technology. Accordingly, the transceiver 140 enables the device 100 to communicate with another device that is separate from device 100. For example, the transceiver 140 may enable device 100 to communicate with a computer, wearable device (such as a smart watch), a cellular phone, and/or any other device that is separate from device 100. The transceiver 140 may communicate over a wide area network such as the Internet or a cellular network, over a local area network, and/or over body area network, for example.

For example, in some aspects, device 100 may communicate with a wireless network. In some aspects, the network may comprise a body area network or a personal area network (e.g., an ultra-wideband network). In some aspects, the network may comprise a local area network or a wide area network. Device 100 may support or otherwise use one or more of a variety of wireless communication technologies, protocols, or standards such as, for example, 3G, LTE, Advanced LTE, 4G, 5G new radio (NR), narrowband IoT (NB-IoT), CDMA, TDMA, OFDM, OFDMA, WiMAX, and Wi-Fi. Similarly, the device 100 may support or otherwise use one or more of a variety of corresponding modulation or multiplexing schemes. The device 100 may wirelessly communicate with other mobile devices, cell phones, other wired and wireless computers, Internet web sites, etc.

In some aspects, the device 100 is a dedicated augmented reality (AR) device, game device, or other device with AR processing and display capabilities. The device 100 described herein may be used in a variety of environments (e.g., shopping malls, streets, offices, homes or anywhere a user may use their device). Users can interface with multiple features of their device 100 in a wide variety of situations. In an AR context, a user may use their device to view a representation of the real world through the display of their device. A user may interact with their AR capable device by using their device's image sensor to receive real world images/video and process the images in a way that superimposes additional or alternate information onto the displayed real world images/video on the device. As a user views an AR implementation on their device, real world objects or scenes may be replaced or altered in real time on the device display. Virtual objects (e.g., text, images, video) may be inserted into the representation of a scene depicted on a device display.

Figure 2:
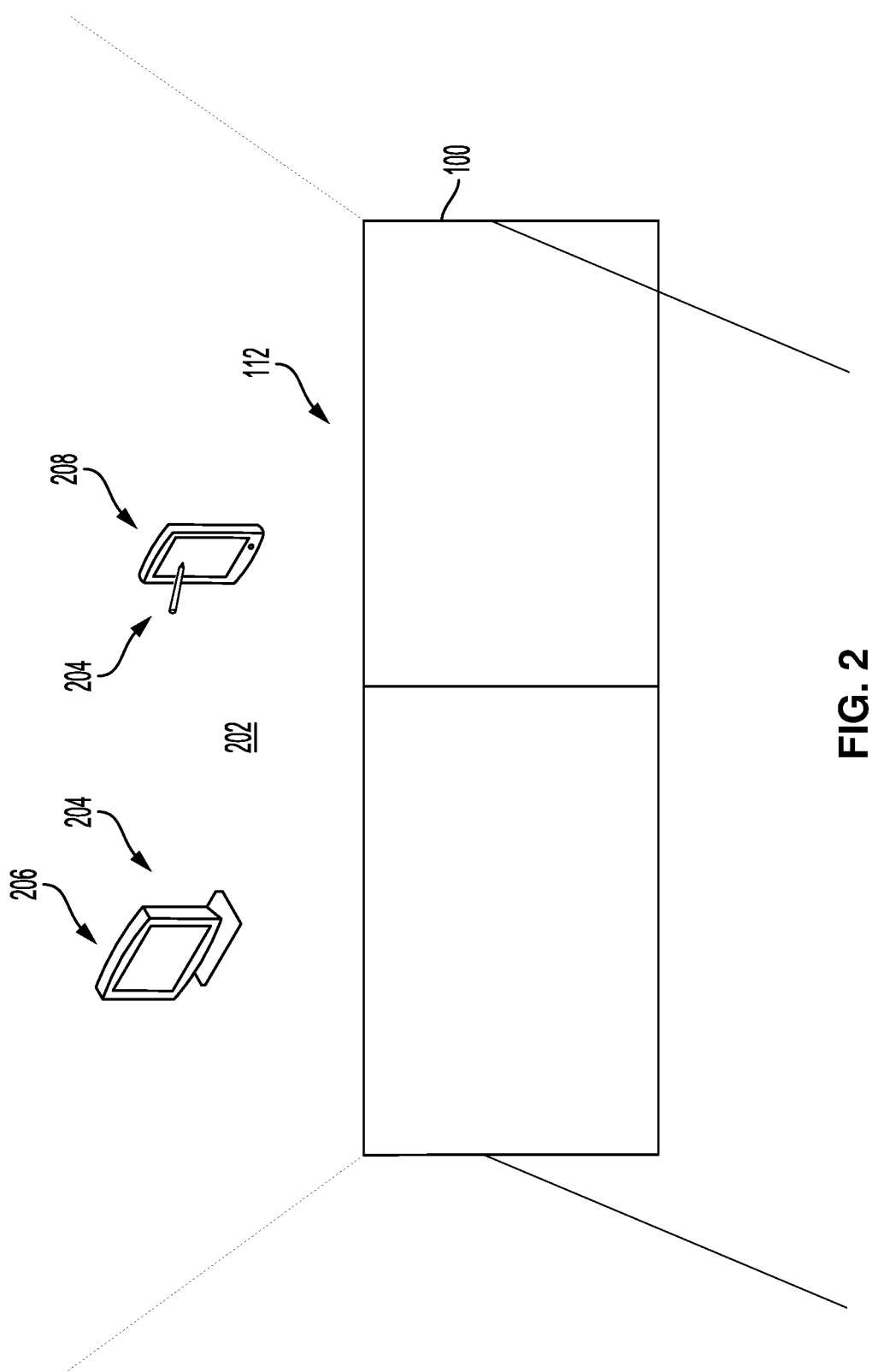
FIG. 2 is a perspective view illustrating a field of view of the device of FIG. 1.

FIG. 2 illustrates a field of view (FOV) 202 of the AR device 100. While the FOV 202 is described herein as being the FOV of the device 100, the FOV 202 is also correlated with the FOV of the user in the examples described herein when the device 100 is worn or used by the user. Accordingly, the FOV described herein refers to both the FOV of the device 100 and the FOV of the user while the user is wearing the device 100.

In the example shown in FIG. 2, a plurality of displays 204 are within the FOV 202 of the device 100 during one or more periods of time. The displays 204 may include, for example, one or more computer monitors, televisions, smart phones, cellular phones, personal digital assistants (PDAs), tablet computing devices (also referred to as tablets), and the like. The displays 204 may be light-emitting displays when the displays are powered on, for example, such that the devices emit light. In one example, during a first period of time, a computer monitor 206 may be within the FOV 202 of the device 100 as the user interacts with the computer. During a second period of time, a tablet 208 may be within the FOV 202 as the user interacts with the tablet 208.

Each display 204 may emit light that reaches the user's eyes during the time the user is looking at the display and/or during the time that the display is within the FOV 202 of the device 100. Accordingly, the device 100 detects the presence of each display 204 within the FOV 202 of the device 100. The device 100 may detect the presence of displays 204 in a variety of ways.

Figure 4:
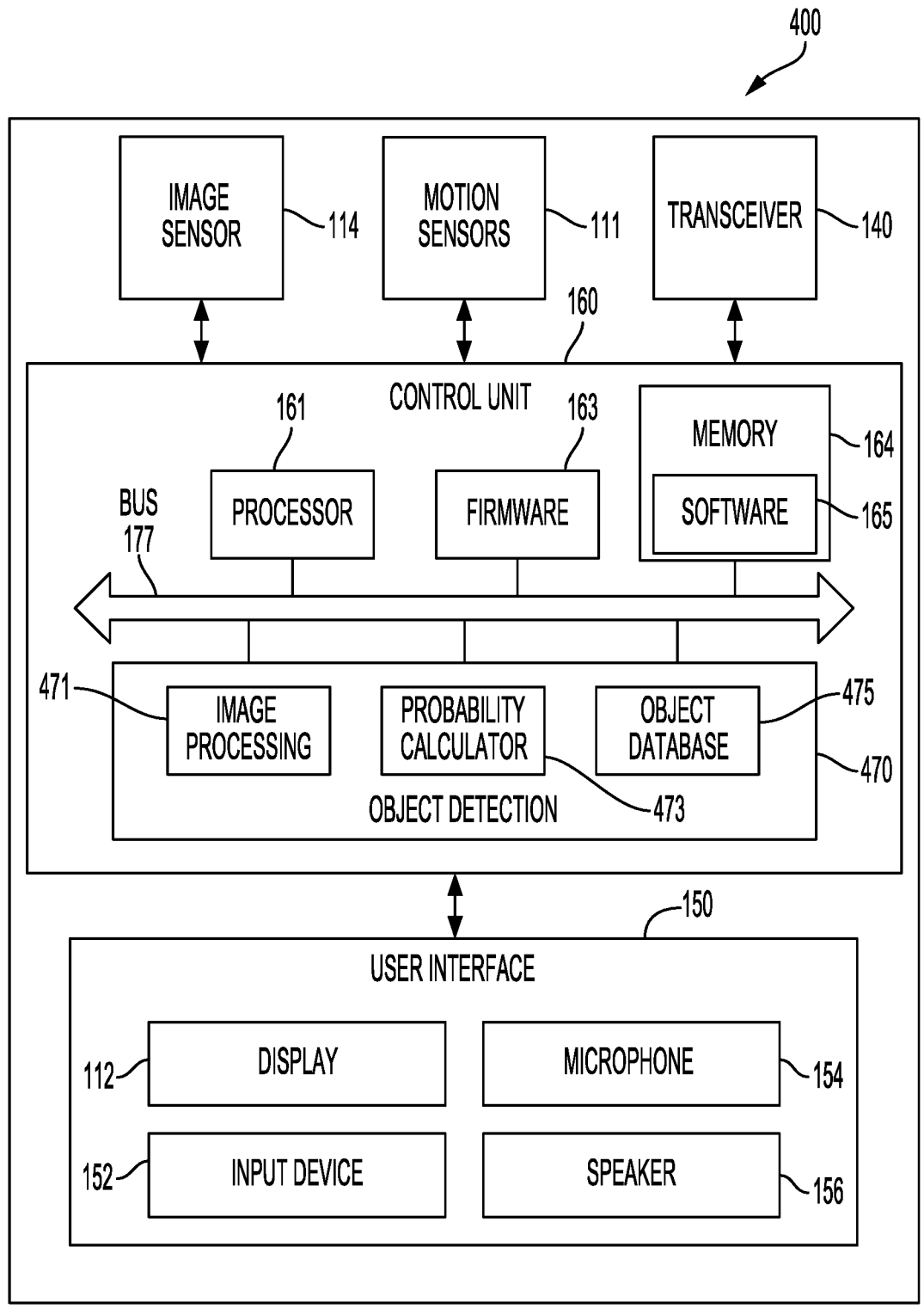
FIG. 4 is a block diagram of another device that may incorporate aspects of the disclosure.
Figure 5:
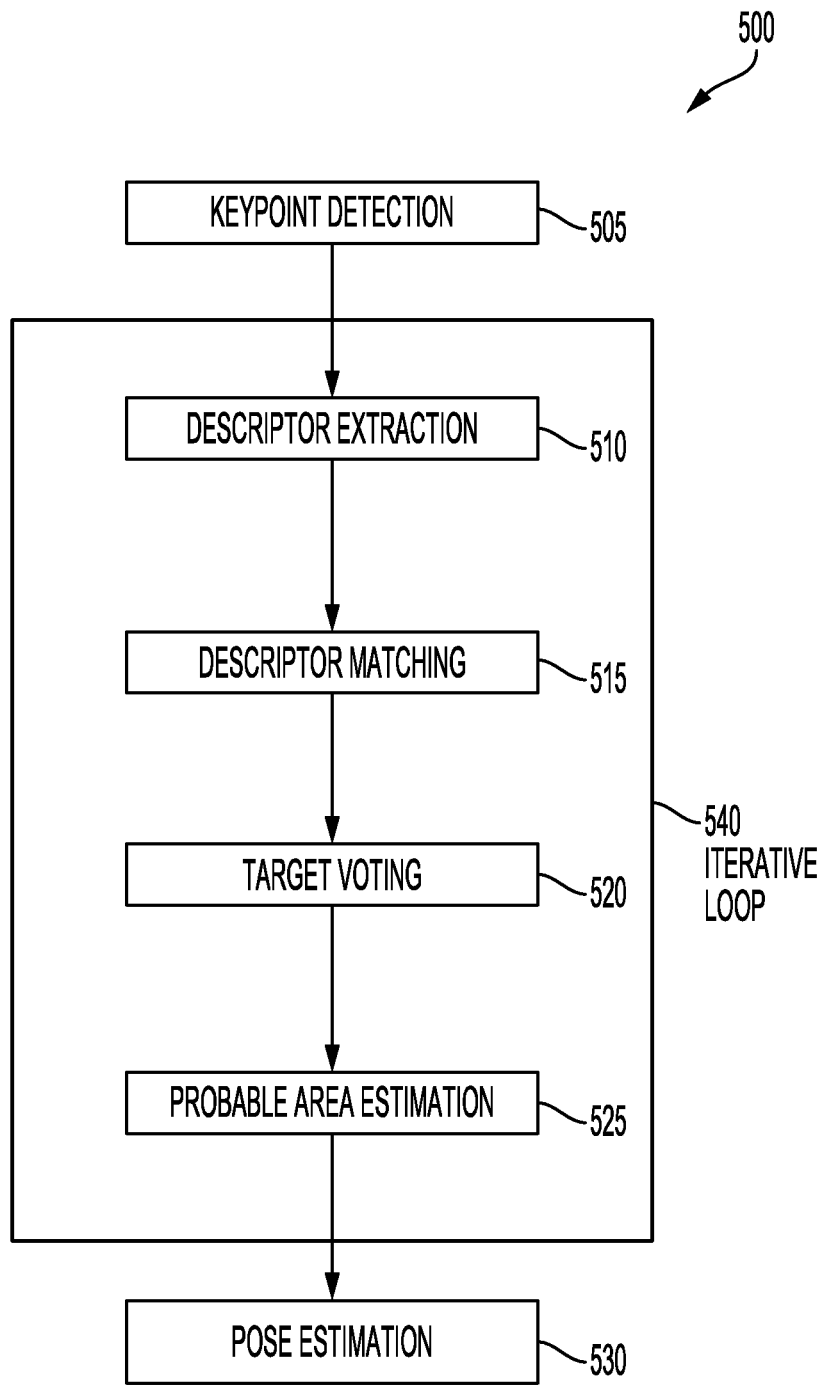
FIG. 5 is a flowchart of a method of detecting objects that may be used with the device of FIG. 4.
Figure 6:
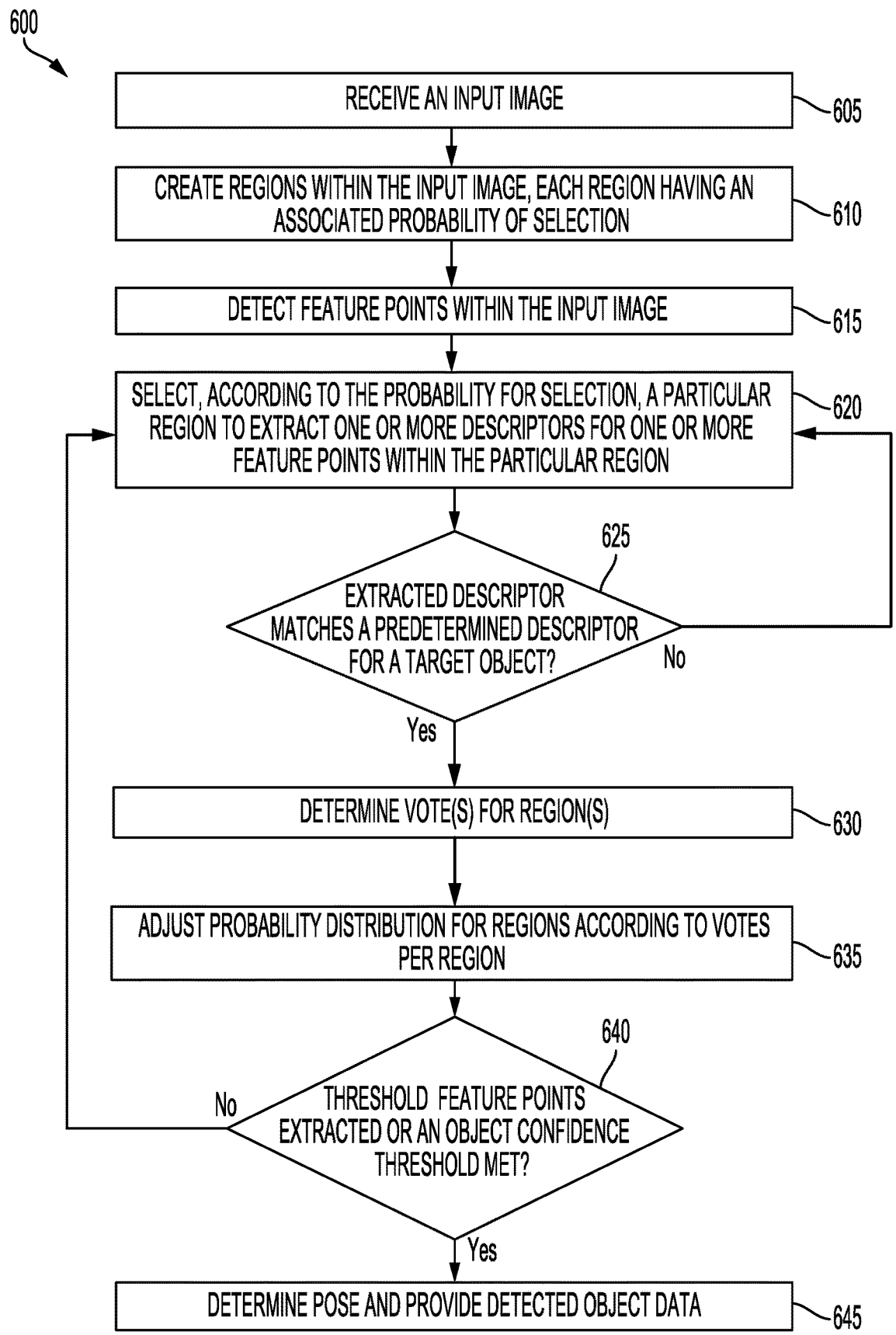
FIG. 6 is a flowchart of another method of detecting objects that may be used with the device of FIG. 4.

A first technique that the device 100 may use to detect the presence of displays is using computer vision techniques such as those described in FIGS. 4-6. A second technique that the device 100 may use to detect the presence of displays is using a blue light sensor as described in FIG. 7. It should be recognized that the device may use both techniques together (e.g., computer vision techniques and blue light detection techniques) to determine whether and how long each display is within the FOV 202 of the device 100.

As described more fully herein, in one aspect, device 100 determines an eye strain indicator based on a cumulative amount of time that each display 204 is detected within the FOV 202 of the device during a monitoring period. More specifically, in one aspect, the device 100 may calculate an amount of time that each display 204 is within the FOV within the monitoring period and may sum the amounts of time to determine the cumulative amount of time that the displays were within the FOV of the device during the monitoring period. In one example, the monitoring period is one day. In another example, the monitoring period is one hour. Alternatively, the monitoring period may be any other suitable period of time, such as six hours, twelve hours, from sunrise to sunset, one week, etc.

The eye strain indicator may then be determined based on the cumulative amount of time. The eye strain indicator may be a numeric value (e.g., from 1 to 100 or from another suitable range of numbers), an alphabetic value (e.g., from A to Z), an alphanumeric number, a color on a color scale (e.g., from blue to red), a symbol (e.g., an image of an eye), text, an audible alert, a haptic alert, and/or any other suitable indicator. The eye strain indicator may then be provided to the user as described more fully herein.

Figure 3:
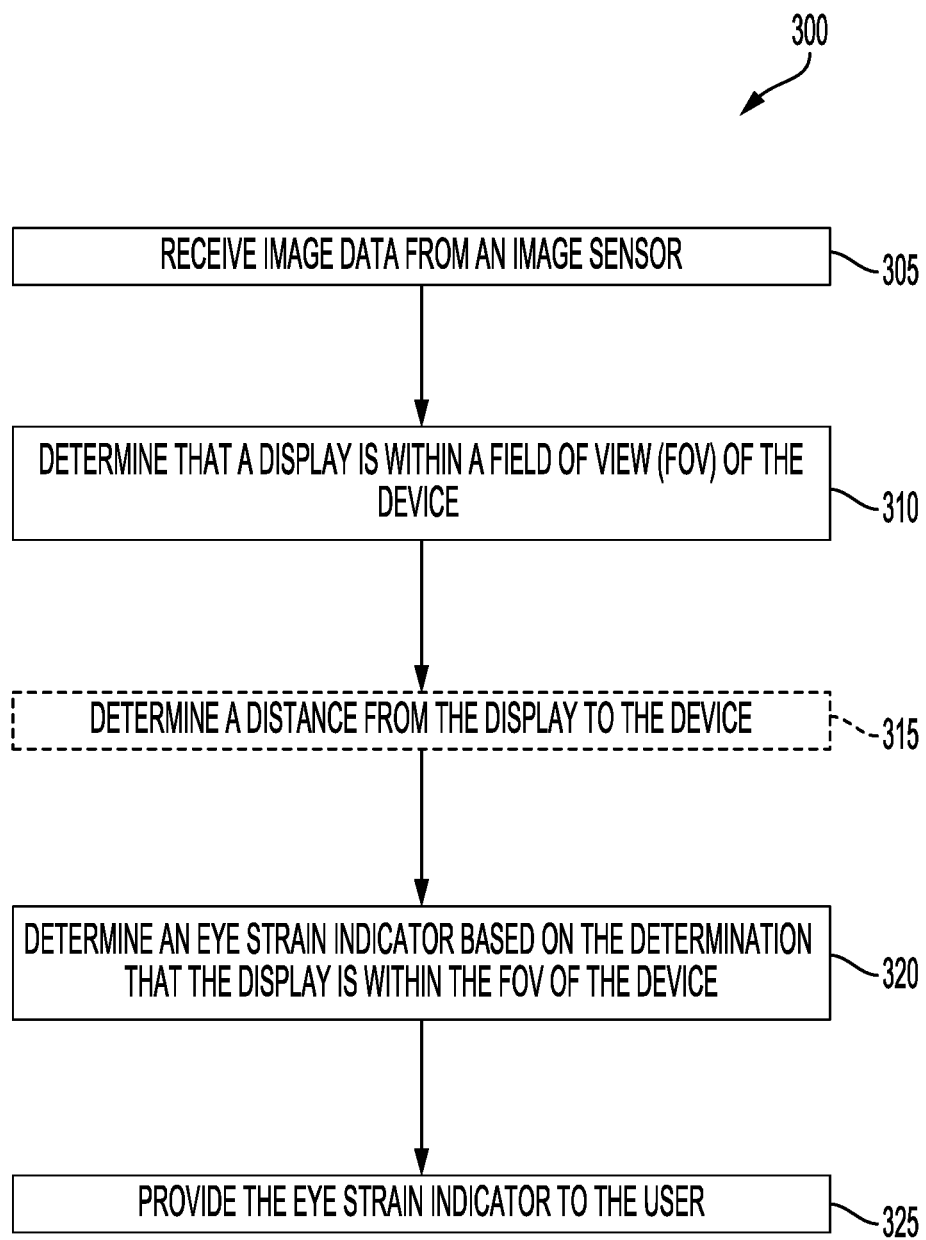
FIG. 3 is a flowchart of a method of determining an eye strain indicator that may be used with the device of FIG. 1.

FIG. 3 is a flowchart of an example method 300 of determining an eye strain indicator based on multiple devices. For example, device 100 (shown in FIG. 1) may determine an eye strain indicator based on the detection of multiple displays within a field of view (FOV) of the device during a monitoring period. In some aspects, method 300 is performed by a processor 161 of device 100 executing instructions stored within a memory of the device 100.

In block 305, the processor 161 receives image data from the image sensor 114 of device 100. Accordingly, the processor 161 may be a means for receiving image data from the image sensor.

More specifically, in one embodiment, a user may wear or otherwise operate device 100. During operation of the device 100, the image sensor 114 may be continuously or periodically active such that image data may be continuously or periodically produced by the image sensor 114. The image sensor 114 may then transmit the image data to the processor 161. In one aspect, if a display is not detected within a FOV of the device 100 (e.g., as set forth in block 310) for a threshold period of time, the image sensor 114 may be deactivated. The image sensor 114 may be reactivated when a device is detected by a blue light sensor, after another threshold period of time has elapsed, upon activation by the user, or another suitable triggering event.

At block 310, the processor 161 may determine that a display (such as display 204 shown in FIG. 2) is within a FOV (such as FOV 202 shown in FIG. 2) of the device 100. Accordingly, the processor 161 may be a means for determining that a display is within a FOV of the device 100. While block 310 references determining that a display is within a FOV of the device 100, it should be recognized that block 310 may also be used to determine that a plurality of displays are within the FOV of the device 100 at a particular time or at various times throughout a period of time.

In one aspect, the processor 161 may use computer vision techniques (e.g., as described in FIGS. 4-6) to determine whether one or more displays 204 are within the FOV of the device. In another aspect, the processor 161 may receive signals and/or data indicative of an amount of blue light detected by a blue light sensor (e.g., as described in FIG. 7). The processor 161 may receive the signals and/or data from the blue light sensor to determine whether one or more displays are within the FOV of the device. In a further aspect, the processor 161 may use both techniques (e.g., computer vision and a blue light sensor) to determine whether one or more displays are within a FOV of the device.

In addition, processor 161 determines an amount of time that each display 204 is within the FOV of the device. For example, processor 161 may initiate a timer when a display 204 is determined to be within the FOV as set forth in block 310. Processor 161 may end the timer when processor 161 determines that the display is no longer within the FOV of the device. The difference between the time that the timer was ended and the time that the timer was initiated may be the amount of time that the display was determined to be within the FOV of the device.

At block 315, the processor 161 optionally determines a distance from the display 204 to the device 100. In one example, the processor 161 may determine a distance from the display 204 to the device 100 using a time-of-flight (ToF) measurement based on transmitting a signal to the display 204 (such as a light signal) and determining a time that has elapsed when a reflected signal is received at the device 100 from the display 204. Block 315 may be used in situations where the device 100 uses computer vision techniques, rather than a blue light sensor, to determine whether a display is within the FOV of the device. As light is generally scattered from an emission source in a variety of directions, less light will generally be received by the user as the user is further away from the display. Accordingly, a display that is further away is expected to cause a lesser amount of light (including blue light) to be received by the user as compared to a display that is closer to the user. As such, the distance from the display to the device may be included in the determination of the eye strain indicator in some aspects as discussed below.

At block 320, the processor 161 determines an eye strain indicator based on the determination that the display is within the FOV of the device. More specifically, the processor 161 may determine the eye strain indicator based on the amount of time that the display is determined to be within the FOV of the device. In an example in which multiple displays are determined to be within the FOV of the device, the processor 161 may determine a cumulative amount of time that all displays were within the FOV of the device during a period of time (e.g., during the monitoring time described above). As noted above, the eye strain indicator may also use the determined distance from the display to the device to when determining the eye strain indicator. Accordingly, if a first display was determined to be within the FOV of the device for 1 hour, and a second device was determined to be within the FOV of the device for 2 hours, the processor 161 may determine that the two displays were within the FOV of the device for a cumulative time of 3 hours during an example monitoring period of 24 hours.

In another aspect in which a blue light sensor is used to determine that one or more displays are within the FOV of the device, the processor 161 may determine the eye strain indicator based on a cumulative amount of blue light detected from each display within the FOV during the monitoring period.

At block 325, the processor 161 provides the eye strain indicator to the user. As discussed above, the eye strain indicator may be a numeric value (e.g., from 1 to 100 or from another suitable range of numbers), an alphabetic value (e.g., from A to Z), an alphanumeric number, a color on a color scale (e.g., from blue to red), a symbol (e.g., an image of an eye), text, an audible alert, a haptic alert, and/or any other suitable indicator. Accordingly, the processor 161 may provide the eye strain indicator to the user by activating a motor or other mechanism to provide the haptic alert to the user. The processor 161 may alternatively activate a speaker or other mechanism to provide the audible alert to the user.

In other aspects, the processor 161 may provide the eye strain indicator for display to the user or for presentation to the user in another form. For example, in one aspect, the processor 161 may display the eye strain indicator on the display 112 of the device 100. Alternatively, the processor 161 may provide the eye strain indicator as an audible or haptic alert to the user via the device 100. In another aspect, the processor 161 may transmit the eye strain indicator to another device that is separate from device 100. The other device may include a computer in which the eye strain indicator is displayed on a computer monitor, a wearable device such as a smartwatch in which the eye strain indicator is displayed on a display of the watch, etc.

FIG. 4 is a block diagram of a device 400 that may be used to determine one or more displays within a FOV of the device. Device 400 is substantially similar to device 100 (shown in FIG. 1) except as otherwise described, and similar components are numbered in FIG. 4 with the same reference numerals used in FIG. 1. In the example shown in FIG. 4, the device 400 is an augmented reality (AR) device 400. The device 400 may be a device that is wearable over the eyes of the user, such as smart eyeglasses, headgear, or the like. Alternatively, the device may be worn or held by the user in such a way that the device is able to detect objects within the field of view of the user.

The device 400 may include a control unit 160 that includes a processor 161 and a memory 164 coupled to one or more busses 177 or signal lines, as well as an object detection system 470 that includes an image processing module 471, a probability calculator 473, and an object database 475. The object detection system 470 is illustrated as a separate component from the processor 161 and memory 164 in FIG. 4. However, it should be recognized that the object detection system 470 (or one or more components within object detection system 470) may be combined and/or implemented in the processor 161 based on instructions stored in software 165 and/or firmware 163. The processor 161 may cause the object detection system 470 to perform computer vision techniques and/or other forms of object detection to detect one or more objects (such as displays) within a field of view (FOV) of the device 400 as described more fully herein.

The device 400 can include a means for capturing an image and generating resulting image data, such as image sensor 114. The image sensor 114 may be incorporated into a front-facing camera in some aspects. The device 400 may optionally include motion sensors 111, such as accelerometers, gyroscopes, electronic compass, or other similar motion sensing elements. In one embodiment, image sensor 114 produces an input image for the object detection system 470 as described herein. Furthermore, as an illustrative example, memory 164 may store instructions which when executed by processor 161, can create regions of interest in the input image, can select according to probability, a particular region, can analyze properties of regions, and update probabilities for the regions.

The device 400 may further include a user interface 150 that includes a means for displaying an augmented reality image, such as the display 112. The user interface 150 may also include an input device 152, such as a keyboard, keypad, gesture recognition system, or other input device through which the user can input information into the device 400. The user interface 150 may also include a microphone 154 and speaker 156. Device 400 may include other components not illustrated in FIG. 4, such as a satellite position system receiver, power device (e.g., a battery), as well as other components typically associated with portable and non-portable electronic devices.

The device 400 may include a transceiver 140 that may communicate via one or more wireless communication links through a wireless network based on or otherwise supporting any suitable wireless communication technology. Accordingly, the transceiver 140 enables the device 400 to communicate with another device that is separate from device 400. For example, the transceiver 140 may enable device 400 to communicate with a computer, wearable device (such as a smart watch), a cellular phone, and/or any other device that is separate from device 400. The transceiver 140 may communicate over a wide area network such as the Internet or a cellular network, over a local area network, and/or over body area network, for example.

For example, in some aspects, device 400 may communicate with a wireless network. In some aspects, the network may comprise a body area network or a personal area network (e.g., an ultra-wideband network). In some aspects, the network may comprise a local area network or a wide area network. Device 400 may support or otherwise use one or more of a variety of wireless communication technologies, protocols, or standards such as, for example, 3G, LTE, Advanced LTE, 4G, 5G new radio (NR), narrowband IoT (NB-IoT), CDMA, TDMA, OFDM, OFDMA, WiMAX, and Wi-Fi. Similarly, the device 400 may support or otherwise use one or more of a variety of corresponding modulation or multiplexing schemes. The device 400 may wirelessly communicate with other mobile devices, cell phones, other wired and wireless computers, Internet web sites, etc.

FIG. 5 is a flowchart of an example method 500 of object detection. In one aspect, the method 500 is implemented by device 400. In a further aspect, the method 500 is implemented by the object detection system 470 as executed by the processor 161. The method 500 described with reference to FIG. 5 is one example of a method of detecting objects, such as displays, within a FOV of the device 400. However, it should be recognized that other suitable computer vision or machine learning techniques may be used in addition to, or in place of, method 500 to detect objects within the FOV of device 400.

As illustrated in FIG. 5, the object detection system 470 may perform keypoint detection on an image received from an image sensor (such as image sensor 114) at block 505. For example, image processing module 471 may identify or extract keypoints from the image using a Hessian Affine, a Harris Affine, a Hessian Laplace, or a MSER detection method. It should be recognized that any other suitable keypoint detection method may be used instead, however.

At block 510, the object detection system 470 may perform descriptor extraction. For example, the object detection system 470 may extract descriptors from features within image sensor images. A feature (e.g., feature point or interest point) as used herein is as an interesting or notable part of an image. Feature detection may be an image processing operation to examine every pixel to determine whether a feature exists at a particular pixel. Feature detection may process an entire captured image or, alternatively certain portions or parts of the captured image. The descriptors extracted from the features of the captured image may represent distinct points along three-dimensional space (e.g., coordinates on axes X, Y, and Z) and every feature point may have an associated feature location. For each captured image or video frame, once features have been detected, a local image patch around the feature can be extracted. Features may be extracted using a technique such as Scale Invariant Feature Transform (SIFT), which localizes features and generates their descriptions. If desired, other techniques, such as Speed Up Robust Features (SURF), Gradient Location-Orientation histogram (GLOH), Normalized Cross Correlation (NCC) or other comparable techniques may be used. When the number of extracted features for an image is determined to exceed a threshold (e.g., 100 point features or other number of points) the image and features can be saved as a keyframe.

At block 515, the embodiment performs descriptor matching. The extracted descriptors for features may either match or fail to match (i.e., are the same or correspond to) the features of previously captured images. For example, the previously captured images may be images stored in an object database such as object database 475.

At block 520, the embodiment performs target voting using, in one example, probability calculator 473 or another suitable component of object detection system 470. For example, target voting may include segmenting an image into regions and separately voting or determining confidence that a target object is present within the respective region. In some embodiments, direction to center vectors are determined within a respective region and votes or confidence for a region occurs when the vectors intersect each other, or intersect the respective region. In other embodiments, votes or confidence is increased when an extracted descriptor within the region matches the descriptor of the target object in a database.

At block 525, the embodiment performs probable area estimation using, in one example, probability calculator 473 or another suitable component of object detection system 470. For example, using a biased Monte Carlo probability distribution, votes for high likelihood regions will increase the probability of selecting those areas in a future descriptor extraction iteration. As illustrated blocks 510-525 may iterate for two or more iterations. For example, in response to voting and updating probabilities, additional descriptors are extracted and matched with a reference database so that additional voting and updating of probabilities may occur. In one embodiment, iterative loop 540 may repeat until a threshold number of descriptors are extracted (e.g., per region or per image), or the object is detected/not-detected within a threshold confidence.

At block 530, the embodiment estimates pose. In one embodiment, in response to detecting the object with high confidence, the object detection system 470 initiates pose estimation of the object. In some embodiments, estimating pose, the object detection system 470 triggers and/or sends appropriate data for tracking for the object to a tracking system (e.g., SLAM).

The method 500 therefore may be used by device 400 to detect displays 204 within the FOV of the device and to detect the pose of the display 204. In such a manner, the device 400 may determine that a display is oriented toward the device (and thus toward the user) such that light is being emitted toward the user's eyes, or to determine that the display is oriented away from the device (and thus away from the user) such that light is being emitted away from the user's eyes. Accordingly, the device may take the pose of the display into account when determining the eye strain indicator. More specifically, in one aspect, the device 400 may ignore, or may apply a reduced weight to, displays that are oriented away from the user such that those displays do not contribute to the eye strain indicator as much as displays that are oriented toward the user.

FIG. 6 is a flowchart illustrating another example method 600 of object detection. In one aspect, the method 600 is implemented by device 400. In a further aspect, the method 600 is implemented by the object detection system 470 as executed by the processor 161. The method 600 described with reference to FIG. 6 is one example of a method of detecting objects, such as displays 204, within a FOV of the device 400. However, it should be recognized that other suitable computer vision or machine learning techniques may be used in addition to, or in place of, method 600 to detect objects within the FOV of device 400.

At block 605, the object detection system 470 receives an input image (also referred to as image data). For example, image sensor 114 generates an image based on light incident on the image sensor and transmits the image (i.e., the image data) to the processor 161. The processor 161 may then transmit the image to the object detection system 470.

At block 610, the object detection system 470 creates regions within the input image, each region having an associated probability of selection. For example, the image may be initialized with an equal probability of selecting each region. In some embodiments, the arrangement of the regions may be superpixel based, equal sized, or based on a depth map. Other region/segment arrangements are also possible.

At block 615, the object detection system 470 detects feature points within the input image. In some embodiments, a threshold number of feature points are detected and used to start the object detection process. The number of feature points to detect may be determined per image or per region. In some embodiments, the object detection system 470 receives a keyframe image that includes detected feature points.

At block 620, the object detection system 470 selects, according to the probability for selection, a particular region to extract one or more descriptors for one or more feature points within the particular region. In some embodiments, before a first descriptor extraction all regions may have an equal probability of being selected. In other embodiments, features are ranked according to strength and stronger features receive a higher probability of selection. If all regions are equally probable for section, during a first iteration, the object detection system 470 may randomly select one or more regions to extract descriptors. In some embodiments, the object detection system 470 may begin by extracting two (or some other configurable number) descriptors within each region or a number from just one first region and then proceed to determining whether the descriptors have a match at block 625. In some embodiments, during subsequent iterations, the number of descriptors extracted may vary depending on the number of votes for the particular region. For example, the object detection system 470 may determine that once a threshold number of votes are received for a region, that all feature points should be used to extract descriptors within the region. In other embodiments, the number of extracted descriptors remains constant for each iteration.

At block 625, the object detection system 470 determines whether the extracted descriptor matches a predetermined descriptor for a target object (e.g., display 204). If there is a match, the embodiment continues to block 630. Otherwise, the method 600 returns to block 620.

At block 630, the object detection system 470 determines vote(s) for region(s). In one embodiment, for each descriptor matching a reference descriptor, the object detection system 470 determines a dominant direction vector for the descriptor's associated feature point and determines a direction and distance vector relative to the dominant direction. In response to determining a direction and distance vector, the object detection system 470 can increment a particular region vote when the region contains (e.g., bounds, encapsulates, etc.) two intersecting direction vectors. In some embodiments, the direction and distance vector may extend beyond the particular region, in which case if the intersection of the newly formed direction and distance vector intersects a second region other than the particular region, the second region may receive a vote.

In one embodiment, a particular region (e.g., current, or currently selected) receives a vote or increased confidence when a direction vector intersects the particular region. For example, if a newly created direction and distance vector intersects with a section of the particular region, the particular region receives a vote. In some embodiments, if the newly created direction and distance vector intersects with a section/portion of a second (or third, or more) region(s) the respective region(s) receive a vote. For example, the second or more region(s) may be adjacent or nearby to the particular region containing the descriptor when they are intersected by a region. In some embodiments, each respective region intersected by the direction and distance vector will receive a vote for the respective region. Therefore, in some embodiments, creating/determining a single direction and distance vector may cause multiple regions to receive votes.

In one embodiment for a particular (e.g., current, or currently selected from block 620) region, a vote is counted for the particular region in response to determining the descriptor matches a predetermined descriptor in a reference database.

At block 635, the object detection system 470 adjusts a probability distribution for regions according to votes per region. For example, the object detection system can recalculate probabilities according to all the newly acquired votes (if any) from block 630.

At block 640, the object detection system 470 determines whether a threshold number of feature points are extracted or an object confidence threshold has been met. If either or both conditions are met, the object detection system 470 continues to a next image and provides data for pose estimation if possible. Otherwise, the object detection system 470 continues to extract descriptors by selecting regions according to probability. In some embodiments, after estimating pose, the object detection system 470 may ignore the detected object region for subsequent images since tracking of the object may occur in a separate dedicated process. Furthermore, the probability distribution for a first image may be carried forward to a second image. After a threshold time period, the object detection system may fully reset all region probabilities.

At block 645, the object detection system 470 determines pose and provides detected object data. For example, pose may be estimated with Random sample consensus (RANSAC) and three point poses using the subset of correspondences that fit the hypothesis (i.e. votes for the object center). The processor 161 may then determine an eye strain indicator based on the detection of the object and/or based on the pose as described above.

Figure 7:
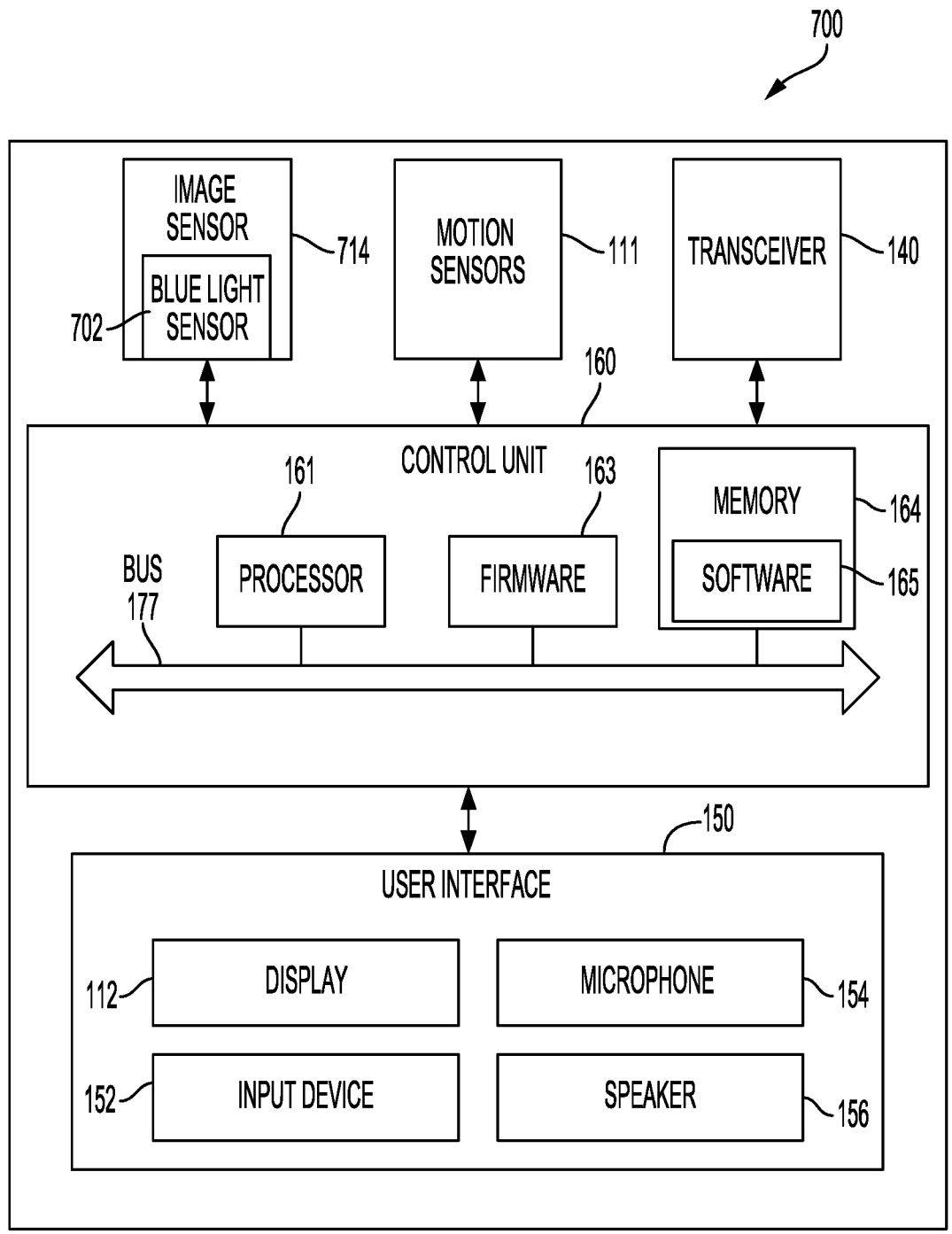
FIG. 7 is a block diagram of another device that may incorporate aspects of the disclosure.

FIG. 7 is a block diagram illustrating an example device 700. Device 700 is substantially similar to device 100 (shown in FIG. 1) except as otherwise described, and similar components are numbered in FIG. 7 with the same reference numerals used in FIG. 1. In the example shown in FIG. 7, the device 700 is an augmented reality (AR) device 700.

The device 700 may be a device that is wearable over the eyes of the user, such as smart eyeglasses, headgear, or the like. Alternatively, the device may be worn or held by the user in such a way that the device is able to detect objects within the field of view of the user. The device 700 may include a control unit 160 that includes a processor 161 and a memory 164 coupled to one or more busses 177 or signal lines. Control unit 160 can be configured to implement methods of performing object detection as described herein. For example, the control unit 160 can be configured to implement functions of device 700 for detecting displays within a field of view of the device 700.

The device 700 can include a means for capturing an image and generating resulting image data, such as image sensor 714. The image sensor 714 may be incorporated into a front-facing camera in some aspects. The device 700 may optionally include motion sensors 111, such as accelerometers, gyroscopes, electronic compass, or other similar motion sensing elements. Furthermore, as an illustrative example, memory 164 may store instructions which when executed by processor 161, can create regions in the input image, can select according to probability, a particular region, can analyze properties of regions, and update probabilities for the regions.

The device 700 may further include a user interface 150 that includes a means for displaying an augmented reality image, such as the display 112. The user interface 150 may also include an input device 152, such as a keyboard, keypad, gesture recognition system, or other input device through which the user can input information into the device 700. The user interface 150 may also include a microphone 154 and speaker 156. Device 700 may include other components not illustrated in FIG. 1, such as a satellite position system receiver, power device (e.g., a battery), as well as other components typically associated with portable and non-portable electronic devices.

The device 700 may include a transceiver 140 that may communicate via one or more wireless communication links through a wireless network based on or otherwise supporting any suitable wireless communication technology. Accordingly, the transceiver 140 enables the device 700 to communicate with another device that is separate from device 700. For example, the transceiver 140 may enable device 700 to communicate with a computer, wearable device (such as a smart watch), a cellular phone, and/or any other device that is separate from device 700. The transceiver 140 may communicate over a wide area network such as the Internet or a cellular network, over a local area network, and/or over body area network, for example.

For example, in some aspects, device 700 may communicate with a wireless network. In some aspects, the network may comprise a body area network or a personal area network (e.g., an ultra-wideband network). In some aspects, the network may comprise a local area network or a wide area network. Device 700 may support or otherwise use one or more of a variety of wireless communication technologies, protocols, or standards such as, for example, 3G, LTE, Advanced LTE, 4G, 5G new radio (NR), narrowband IoT (NB-IoT), CDMA, TDMA, OFDM, OFDMA, WiMAX, and Wi-Fi. Similarly, the device 700 may support or otherwise use one or more of a variety of corresponding modulation or multiplexing schemes. The device 700 may wirelessly communicate with other mobile devices, cell phones, other wired and wireless computers, Internet web sites, etc.

In one aspect, device 700 includes a blue light sensor 702 that is configured to detect an amount of blue light received at device 700. The blue light sensor 702 may be integrated within the image sensor 714, or may be implemented as a separate component of device 700. For example, the device 700 may dedicate a portion of the image sensor to detecting blue light. In such an example, the image sensor may include a plurality of pixels that respond to the incidence of blue light on the pixels and that generate a blue light detection signal in response to the incidence of blue light.

Given the fact that blue light is a component of light emitted from a variety of sources including sunlight, the blue light sensor 702 may detect the amount of blue light emitted by each display 204 within the FOV 202 of the device 700, as well as blue light emitted from other sources within the FOV 202 of the device 700. In one aspect, to reduce the impact on the eye strain indicator of blue light from sources other than displays 204 in the FOV 202, the image sensor 714 or another component of the device 700 may further include a blue light threshold circuit or module to only pass along the blue light detection signal to the processor 161 if the amount of blue light detected (i.e., the blue light detection signal) exceeds a blue light detection threshold. Alternatively, the blue light threshold module may be implemented in software such that the processor 161 may filter out or otherwise ignore blue light signals that do not meet or exceed the blue light detection threshold. In such aspects, the processor 161 may determine the eye strain indicator based only on blue light detected from displays within the FOV of the device. In other aspects, the processor may determine the eye strain indicator based on blue light detected from all sources during the monitoring period of time such that the device 700 may inform the user of a total amount of blue light detected from all sources during the monitoring period.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, engines, circuits, and algorithm steps described in connection with the embodiments disclosed herein may be implemented as electronic hardware, computer software, or combinations of both. To clearly illustrate this interchangeability of hardware and software, various illustrative components, blocks, modules, engines, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more exemplary embodiments, the functions, modules, and/or methods described may be implemented in hardware (e.g., control unit 160), software (e.g., software 165), firmware (e.g., firmware 163), or any combination thereof. If implemented in software as a computer program product, the functions, modules, and/or methods may be stored on or transmitted over as one or more processor-executable instructions or code in a non-transitory computer-readable medium. Non-transitory computer-readable media can include computer storage media, such as any available media that can be accessed by a computer, or data processing device/system. By way of example, and not limitation, such non-transitory computer-readable media can comprise Random Access Memory (RAM), Read Only Memory (ROM), Electrically Erasable Programmable Read-Only Memory (EEPROM), Compact Disc Read Only Memory (CD-ROM) or other optical disk storage, magnetic disk storage or other magnetic storage devices, or any other medium that can be used to carry or store desired program code in the form of instructions or data structures and that can be accessed by a computer. Combinations of the above should also be included within the scope of non-transitory computer-readable media.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An augmented reality (AR) device wearable by a user, the AR device comprising:
   an image sensor;
   a local display; and
   a processor coupled to the image sensor, the processor configured to:
   receive image data from the image sensor;
   detect feature points within the image data;
   select a particular region to extract one or more descriptors for one or more feature points within a region;
   determine whether at least one descriptor within the region matches a remote display;
   determine an amount of time that the remote display is within a field of view (FOV) of the AR device;
   determine an eye strain indicator based on the amount of time that the remote display is within the FOV of the AR device; and
   provide the eye strain indicator to the user.

2. The AR device of claim 1, wherein the image sensor comprises a blue light sensor configured to detect an amount of blue light emitted by the remote display.

3. The AR device of claim 2, wherein the processor is further configured to determine the eye strain indicator based on the amount of blue light detected by the blue light sensor.

4. The AR device of claim 1, wherein the processor is further configured to determine a distance from the AR device to the remote display.

5. The AR device of claim 4, wherein the processor is further configured to determine the eye strain indicator based on the distance from the AR device to the remote display.

6. The AR device of claim 1, wherein the remote display is one of a plurality of remote displays, wherein the processor is further configured to determine that the plurality of remote displays has been within the FOV of the AR device during a period of time, and wherein the processor is further configured to determine the eye strain indicator based on a cumulative amount of time that the plurality of remote displays has been within the FOV of the AR device.

7. The AR device of claim 1, wherein the processor is configured to provide the eye strain indicator by transmitting the eye strain indicator to a device that is separate from the AR device.

8. The AR device of claim 1, wherein the processor is configured to provide the eye strain indicator by displaying the eye strain indicator to the user on the local display.

9. A method of determining an eye strain indicator, the method comprising:
- receiving image data from an image sensor of an augmented reality (AR) device;
- detecting feature points within the image data;
- selecting a particular region to extract one or more descriptors for one or more feature points within a region;
- determining whether at least one descriptor within the region matches a remote display;
- determining an amount of time that the remote display is within a field of view (FOV) of the AR device;
- determining an eye strain indicator based on the amount of time that the remote display is within the FOV of the AR device; and
- providing the eye strain indicator to a user.

10. The method of claim 9, wherein determining that a remote display is within a FOV of an AR device comprises detecting an amount of blue light emitted by the remote display.

11. The method of claim 10, wherein determining an eye strain indicator comprises determining the eye strain indicator based on the amount of blue light detected.

12. The method of claim 9, further comprising determining a distance from the AR device to the remote display.

13. The method of claim 12, wherein determining an eye strain indicator further comprises determining the eye strain indicator based on the distance from the AR device to the remote display.

14. The method of claim 9, wherein the remote display is one of a plurality of remote displays, the method further comprising determining that the plurality of remote displays has been within the FOV of the AR device during a period of time, and wherein determining the eye strain indicator further comprises determining the eye strain indicator based on a cumulative amount of time that the plurality of remote displays has been within the FOV of the AR device.

15. The method of claim 9, wherein providing the eye strain indicator comprises transmitting the eye strain indicator to a device that is separate from the AR device.

16. The method of claim 9, wherein the AR device comprises a local display, and wherein providing the eye strain indicator comprises displaying the eye strain indicator to the user on a local display.

17. An augmented reality (AR) device wearable by a user, the AR device comprising:
- means for generating image data;
- means for receiving the image data;
- means for detecting feature points within the image data;
- means for selecting a particular region to extract one or more descriptors for one or more feature points within a region;
- means for determining whether at least one descriptor within the region matches a remote display;
- means for determining an amount of time that the remote display is within a field of view (FOV) of the AR device;
- means for determining an eye strain indicator based on the amount of time that the remote display is within the FOV of the AR device; and
- means for providing the eye strain indicator to the user.

18. The AR device of claim 17, wherein the means for generating image data comprises a blue light sensor configured to detect an amount of blue light emitted by the remote display.

19. The AR device of claim 18, wherein the means for determining an eye strain indicator is configured to determine the eye strain indicator based on the amount of blue light detected by the blue light sensor.

20. The AR device of claim 17, wherein the means for determining that a remote display is within a FOV of the AR device is configured to determine a distance from the AR device to the remote display.

21. The AR device of claim 20, wherein the means for determining an eye strain indicator is configured to determine the eye strain indicator based on the distance from the AR device to the remote display.

22. The AR device of claim 17, wherein the remote display is one of a plurality of remote displays, wherein the means for determining that a remote display is within a FOV of the AR device is configured to determine that the plurality of remote displays has been within the FOV of the AR device during a period of time, and wherein the means for determining an eye strain indicator is configured to determine the eye strain indicator based on a cumulative amount of time that the plurality of remote displays has been within the FOV of the AR device.

23. The AR device of claim 17, wherein the means for providing an eye strain indicator is configured to transmit the eye strain indicator to a device that is separate from the AR device or to display the eye strain indicator to the user on a local display.

24. A non-transitory computer-readable medium comprising processor-executable instructions stored thereon, wherein when a processor executes the instructions, the processor is configured to:
- receive image data from an image sensor of an augmented reality (AR) device;
- detect feature points within the image data;
- select a particular region to extract one or more descriptors for one or more feature points within a region;
- determine whether at least one descriptor within the region matches a remote display;
- determine an amount of time that the remote display is within a field of view (FOV) of the AR device;
- determine an eye strain indicator based on the amount of time that the remote display is within the FOV of the AR device; and
- provide the eye strain indicator to a user.

* * * * *